(12) United States Patent
Tsuyuki (10) Patent No.: US 6,782,071 B1
(45) Date of Patent: Aug. 24, 2004

(54) MULTI-SLICE X-RAY COMPUTED TOMOGRAPHY APPARATUS

(75) Inventor: Masaharu Tsuyuki, Tochigi-Ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/367,761

(22) Filed: Feb. 19, 2003

(30) Foreign Application Priority Data

Feb. 19, 2002 (JP) .......................................... 2002-040942

(51) Int. Cl.[7] .............................................. G21K 1/00
(52) U.S. Cl. .................................. 378/4; 378/8; 378/20
(58) Field of Search ........................ 378/4, 8, 147–148, 378/95, 20

(56) References Cited

U.S. PATENT DOCUMENTS

| | | | |
|---|---|---|---|
| 5,459,769 A | | 10/1995 | Brown |
| 5,612,985 A | * | 3/1997 | Toki et al. ...................... 378/4 |
| 6,366,638 B1 | * | 4/2002 | Hsieh et al. ..................... 378/4 |

FOREIGN PATENT DOCUMENTS

JP    10-127621    5/1998

\* cited by examiner

Primary Examiner—Edward J. Glick
Assistant Examiner—Hoon Song
(74) Attorney, Agent, or Firm—Oblon, Spivak, McClelland, Maier & Neustadt, P.C.

(57) ABSTRACT

An X-ray computed tomography apparatus, comprises an X-ray generator, an X-ray detector, a controller, and a display. The X-ray generator is configured to generate a first X-ray in a pre-scan mode and a second X-ray in an image scan mode. The X-ray detector is configured to detect a first transmission X-ray exposed through a specimen to a first exposure width of the X-ray detector along a body axis of the specimen, resulting from the first X-ray at a first scanning position in the pre-scan mode. The X-ray detector is further configured to detect a second transmission X-ray exposed through the specimen to a second exposure width of the X-ray detector along the body axis of the specimen, resulting from the second X-ray at a second scanning position in the image scan mode. The first exposure width is narrower than the second exposure width. The controller is configured to control the first scanning position and the second scanning position. The display is configured to display a first image based on the first transmission X-ray detected by the X-ray detector and a second image based on the second transmission X-ray detected by the X-ray detector.

35 Claims, 8 Drawing Sheets

BODY AXIS

BODY AXIS

BODY AXIS

MULTI-SLICE X-RAY COMPUTED TOMOGRAPHY APPARATUS

CROSS-REFERENCE TO RELATED APPLICATION

This application is based upon and claims the benefit of priority from prior Japanese Patent Application No. P2002-40942, filed on Feb. 19, 2002, the entire contents of which are incorporated herein by reference.

FIELD OF THE INVENTION

The present invention relates to an X-ray computed tomography which performs a multi-slice scan for obtaining medical images. The present invention further relates to a method of multi-slice scan in such an X-ray computed tomography apparatus.

BACKGROUND OF THE INVENTION

An X-ray computed tomography apparatus (hereinafter referred to as a CT apparatus) is known to provide images of a medical examination object, such as a patient, (hereinafter referred to as a specimen) based on the intensity of an X-ray transmitted through the specimen. The images provided by the CT apparatus play an important role in a variety of medical practices including a diagnosis of a disease, a treatment, and a medical operation planning. Imaging by the CT apparatus is now being realized using a latest technique, such as, for example, a real-time image reconstruction and a multi-slice scan.

The real-time image reconstruction is a technique of reconstructing a present image by utilizing a part of projection data acquired for the previous image as a part of projection data for the present image. Here, the projection data are data obtained by scanning a predetermined part of the specimen. The scan is realized by rotating an X-ray tube radiating an X-ray and an X-ray detector around the specimen and by obtaining X-ray data transmitted through the specimen. An advantage of the real-time image reconstruction is to display an image based on the reconstructed image nearly at the same time as the scan of data for the image even if a time delay for a display processing is considered. The real-time image reconstruction technique is described in detail in Japanese Patent No. 3090400, for example.

Nowadays, an examination using a contrast agent is performed to enhance a predetermined part of the specimen, by injecting the contrast agent in the specimen. Accordingly, it becomes easier, with a contrast-enhanced image, to recognize a specific organ or a predetermined part inside the body of the specimen and, for example, to determine whether there is a tumor or not. Such a contrast-enhanced image is obtained, for example, by scans in the CT apparatus. Since, however, it takes a little time for the contrast agent to reach a predetermined (or desired) part of the specimen after the injection, it has not been so easy to obtain a preferably contrast enhanced image in the CT apparatus. Sometimes the image may be one before the contrast agent has appropriately reached the predetermined part. Or sometimes the image may be one after the contrast agent has already passed the predetermined part.

Therefore, one of the solutions for the above timing problem is adoption of the real-time image reconstruction technique to such an examination with the contrast agent. The examination may be performed as follows. First, a monitoring scan (hereinafter referred to generally as a pre-scan) is implemented at a position adjacent to the predetermined part of the body. Further, the pre-scan is helpful for monitoring an appearance of the image contrast enhancement. After the image contrast enhancement has appeared in the pre-scan, an image scan is implemented for obtaining a contrast-enhanced image of the predetermined part. Since images may be displayed in the monitor of the pre-scan substantially in real time, using the real-time image reconstruction technique, the image contrast enhancement may appear in real-time, Therefore, it may be possible to see the right time to move on to the image scan.

There seems to be no problem when such a contrast enhancement examination described above is implemented in a single-slice scan in each of the pre-scan and the image scan in a conventional CT apparatus. From another point of view, however, the single-slice scan is not so preferable. This is because it usually takes quite a long time to complete the image scan over a predetermined range of the body of the specimen and causes the specimen to be exposed unnecessarily to a large amount of radiation. As an exemplary solution for this problem, another latest technique is known as a multi-slice scan technique.

The multi-slice scan is a technique of obtaining a plurality of projection data of the specimen in a single rotation scan. Application of the multi-slice scan to the image scan described above can realize a reduction of a great deal of scanning time and of an X-ray exposure to the specimen. On the other hand, however, the pre-scan described above does not require such a multi-slice scan. As explained above, the pre-scan is only for monitoring an appearance of the image contrast enhancement. Therefore, the multi-slice scan is rather problematic to the specimen since the specimen is likely to be exposed to more radiation, compared to the radiation in the single-slice scan.

BRIEF SUMMARY OF THE INVENTION

According to a first aspect of the present invention, there is provided an X-ray computed tomography apparatus, which comprises an X-ray generator configured to generate a first X-ray in a pre-scan mode and a second X-ray in an image scan mode. Additionally, an X-ray detector is used and configured to detect a first transmission X-ray exposed through a specimen to a first exposure width of the X-ray detector along a body axis of the specimen, resulting from the first X-ray at a first scanning position in the pre-scan mode and to detect a second transmission X-ray exposed through the specimen to a second exposure width of the X-ray detector along the body axis of the specimen, resulting from the second X-ray at a second scanning position in the image scan mode. The first exposure width is narrower than the second exposure width Further, the apparatus includes a controller configured to control the first scanning position and the second scanning position, and a display configured to display a first image based on the first transmission X-ray detected by the X-ray detector and a second image based on the second transmission X-ray detected by the X-ray detector.

According to a second aspect of the present invention, there is provided an X-ray computed tomography apparatus, which comprises an X-ray source configured to radiate an X-ray to a specimen, a collimator configured to vary a collimating width, along a body axis of the specimen, which determines a X-ray width exposed to the specimen, and a detector, comprising a plurality of detecting elements along the body axis, configured to detect a transmission X-ray transmitted from the specimen. The apparatus further includes a data acquisition unit, comprising a plurality of data acquisition elements along the body axis, configured to acquire output data of the detector and an implementing unit configured to implement a scan around the specimen with the X-ray source and the X-ray detector. A controller is used and configured to control a scan mode to switch from a monitoring scan to an image scan, and to control the collimator to make the collimating width wider in the image scan than in the monitoring scan. The monitoring scan is for monitoring a CT number in a predetermined region of interest of the specimen. The image scan is for scanning an examining region of the specimen. Additionally, the apparatus includes a reconstruction unit configured to reconstruct a tomography of the specimen based on projection data acquired in the monitoring scan, and also to reconstruct an image of the specimen based on projection data acquired in the image scan.

According to a third aspect of the present invention, there is provided a method of performing a scan in an X-ray computed tomography apparatus. The method begins by generating a first X-ray in a pre-scan mode and detecting with an X-ray detector a first transmission X-ray exposed through a specimen to a first exposure width of the X-ray detector along a body axis of the specimen, resulting from the first X-ray at a first scanning position in the pre-scan mode. Next, the method continues by generating a second X-ray in an image scan mode, displaying a first image based on the first transmission X-ray and detecting with the X-ray detector a second transmission X-ray exposed through the specimen to a second exposure width of the X-ray detector along the body axis of the specimen, resulting from the second X-ray at a second scanning position in the image scan mode The second exposure width is wider than the first exposure width. The method continues by displaying a second image based on the second transmission X-ray, and controlling the first scanning position and the second scanning position.

According to a fourth aspect of the present invention, there is provided a computer program product on which is stored a computer program for performing a scan in an X-ray computed tomography apparatus. The computer program has instructions, which when executed, perform steps comprising generating a first X-ray in a pre-scan mode and detecting with an X-ray detector a first transmission X-ray exposed through a specimen to a first exposure width of the X-ray detector along a body axis of the specimen, resulting from the first X-ray at a first scanning position in the pre-scan mode. The steps continue by generating a second X-ray in an image scan mode, displaying a first image based on the first transmission X-ray, and detecting with the X-ray detector a second transmission X-ray exposed through the specimen to a second exposure width of the X-ray detector along the body axis of the specimen, resulting from the second X-ray at a second scanning position in the image scan mode. The second exposure width is wider than the first exposure width. Finally, the steps continue with displaying a second image based on the second transmission X-ray, and controlling the first scanning position and the second scanning position.

BRIEF DESCRIPTION OF THE DRAWINGS

A more complete appreciation of embodiments of the present invention and many of its attendant advantages will be readily obtained by reference to the following detailed description considered in connection with the accompanying drawings, in which.

DETAILED DESCRIPTION OF THE PREFERRED EMBODIMENTS

Figure 1:
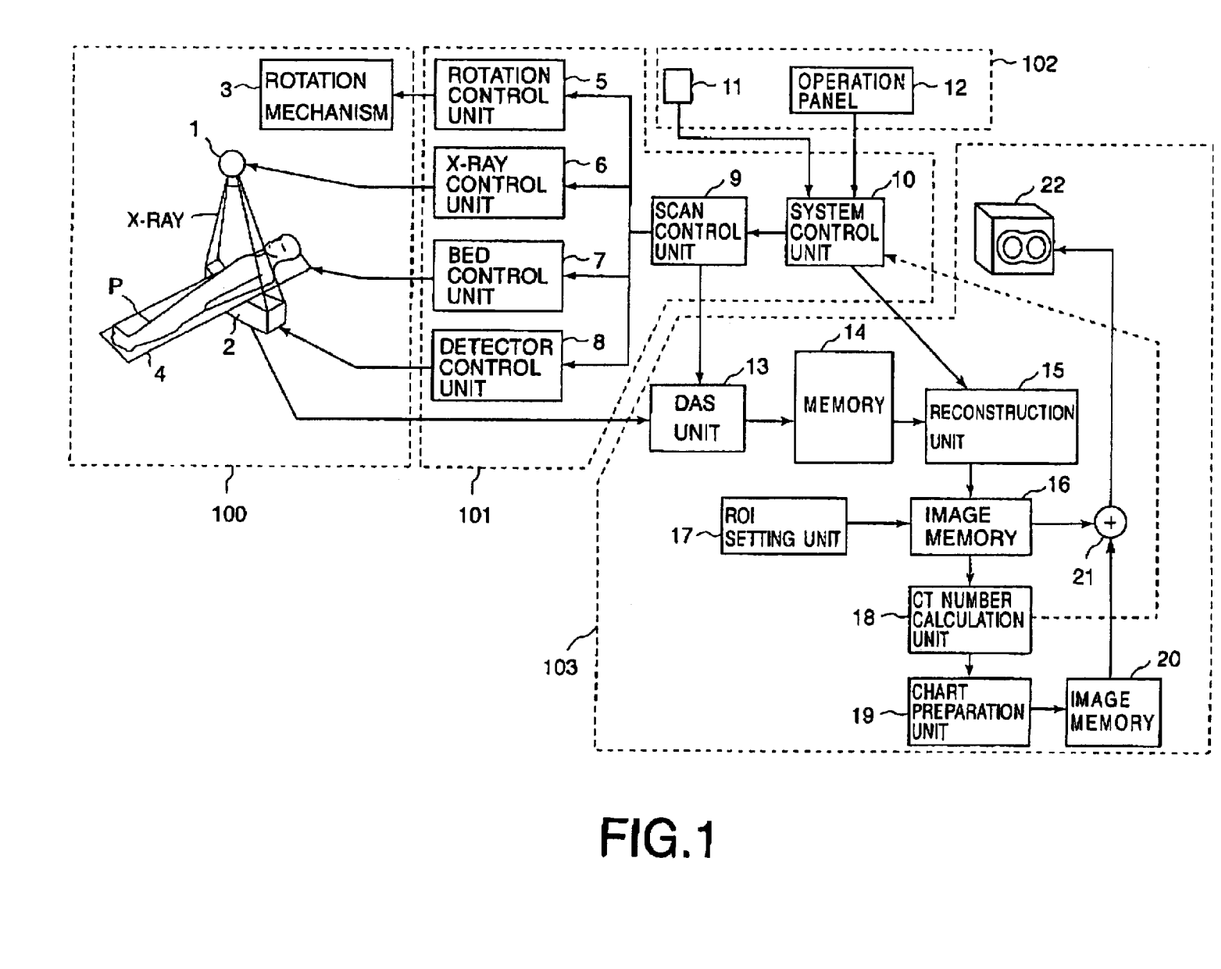
FIG. 1 is a block diagram showing an exemplary configuration of a CT apparatus according to an embodiment of the present invention.

Embodiments of the present invention will be described with reference to the accompanying drawings. FIG. 1 is a block diagram showing an exemplary configuration of a CT apparatus according to an embodiment of the present invention.

The CT apparatus may include a gantry section 100, a control section 101, an operation section 102, and a data processing section 103. The gantry section 100 is for implementing radiography against a specimen, such as a patient, P. The control section 101 is for controlling the gantry section 100, and the data processing section 103, for example. The operation section 102 is for inputting various kinds of information and/or operations by a doctor and/or a radiological technologist (hereinafter referred to as an operator). The data processing section 103 is for data processing including an image reconstruction processing.

The gantry section 100 may include an X-ray tube 1, an X-ray detector 2, a rotation mechanism 3, and a bed 4. The X-ray tube 1 radiates (generates) an X-ray which is exposed to the specimen P lying on the bed 4. The X-ray detector 2 may comprise a plurality of detecting elements aligned in two-dimensions. In more detail, a plurality of detecting elements are provided along a body axis of the specimen P in the X-ray detector 2. Also, there are a plurality of detecting elements along an axis orthogonal with the body axis (hereinafter referred to as channel directions). These detecting elements aligned along the body axis and in the channel directions form the two dimensions. In the following description, unless otherwise mentioned, the explanation will be made only regarding the detecting elements along the body axis. Therefore, the detecting elements regarding another dimension (i.e. the channel direction) are omitted in the following explanation. The X-ray detector 2 detects an X-ray which has been transmitted through the specimen P as a result of the X-ray exposure to the specimen P from the X-ray tube 1. The X-ray detector 2 outputs detected X-ray data. The rotation mechanism 3 holds the X-ray tube 1 and the X-ray detector 2 facing to each other and also at the opposite side of the specimen P each other. The rotation mechanism 3 rotates the X-ray tube 1 and the X-ray detector 2 around the specimen P. The rotation mechanism 3 may usually be fixed at a predetermined position, but may also be movable along the body axis and/or in the channel directions if it is needed. The bed 4 is what the specimen P lies on for an examination. The bed 4 is moved along the body axis and also in the channel directions so that a predetermined part of the specimen P can be positioned appropriately for the examination. The bed 4 is further movable up and down against a floor where the CT apparatus is provided.

The control section 101 may include a rotation control unit 5, an X-ray control unit 6, a bed control unit 7, a detector control unit 8, a scan control unit 9, and a system control unit 10. The rotation control unit 5 controls the rotation mechanism 3 to rotate and stop the rotation. The X-ray control unit 6 controls the X-ray tube 1 to be supplied a power and to radiate an X-ray in a predetermined condition. The X-ray control unit 6 may also control a collimator (described later) to collimate the X-ray radiated from the X-ray tube 1 so as to change an X-ray radiation angle or so that the X-ray (transmitted through the specimen P) is exposed to a predetermined range, particularly to a predetermined exposure width along the body axis, of the X-ray detector 2. The rotation control unit 5 described before or the X-ray control unit 6 may further control a position of the X-ray tube 1 to shift towards the X-ray detector 2 in a direction orthogonal with the body axis. This shift may have a similar effect to the control of the collimator since an X-ray exposure range or width can be changed by the shift.

The bed control unit 7 controls the bed 4 to move in three-dimensional directions. The detector control unit 8 controls the X-ray detector 2 to change detection timings, for example. The scan control unit 9 controls the rotation control unit 5, the X-ray control unit 6, the bed control unit 7, and the detector control unit 8 so that the controls by these control units described before may be accomplished. The scan control unit 9 further controls a DAS unit 13. This control will be described later. The system control unit 10 controls a whole part of the CT apparatus. Especially, the system control unit 10 controls the scan control unit 9. Other control operations by the system control unit 10 will be described later.

The operation section 102 may include a button switch 11 and an. operation panel 12. The button switch 11 is connected with the system control unit 10 and is operative to input a designation that a pre-scan should be terminated. The pre-scan will be described later. The operation panel 12 is connected with the system control unit 10, too. The operation panel 12 is operative to input information regarding, for example, a position of the pre-scan, a condition of the pre-scan, a position of an image scan, a condition of the image scan, and a delay-time from the termination of the pre-scan to the initiation of the image scan. In other words, the delay time is defined as a time difference between the termination of the pre-scan and the initiation of the image scan. The image scan will be explained later.

The data processing section 103 may include the DAS unit 13, a memory 14, a reconstruction unit 15, an image memory 16, an ROI setting unit 17, a CT number calculation unit 18, a chart preparation unit 19, an image memory 20, an adder 21, and an image display 22. Here, DAS stands for data acquisition system. The DAS unit 13 comprises a plurality of data acquisition system elements (hereinafter referred to as DAS elements). The DAS unit 13 acquires data detected and output by the X-ray detector 2 in accordance with a connection between the detecting elements and the DAS elements. The acquisition result may depend on how the detecting elements are connected to the DAS elements. The connection may be controlled or switched by an analog switch. The analog switch will be explained later. The DAS unit 13 outputs acquired data as projection data. The memory 14 stores the projection data output from the DAS unit 13. The reconstruction unit 15 is controlled by the system control unit 10 and performs a reconstruction processing based on the projection data stored in the memory 14 so as to produce reconstructed images (hereinafter referred to as tomographies).

The reconstruction processing by the reconstruction unit 15 is performed substantially in real time. The real time reconstruction may be defined that a tomography T or, more generally, an image is reconstructed based on projection data obtained from a plurality of (the number, enough or necessary for the reconstruction, of) directions around the specimen P, for example, covering 360 degrees around the specimen P within a time less than a time required for acquiring projection data from the number, enough or necessary for the reconstruction of the tomography T, of directions. In practice, one of the examples is a reconstruction processing using projection data which are acquired in first predetermined degrees and projection data already acquired for the previous image. In this case, the projection data for the previous image, from directions corresponding to the first predetermined degrees are not used for the reconstruction processing.

Figure 7:
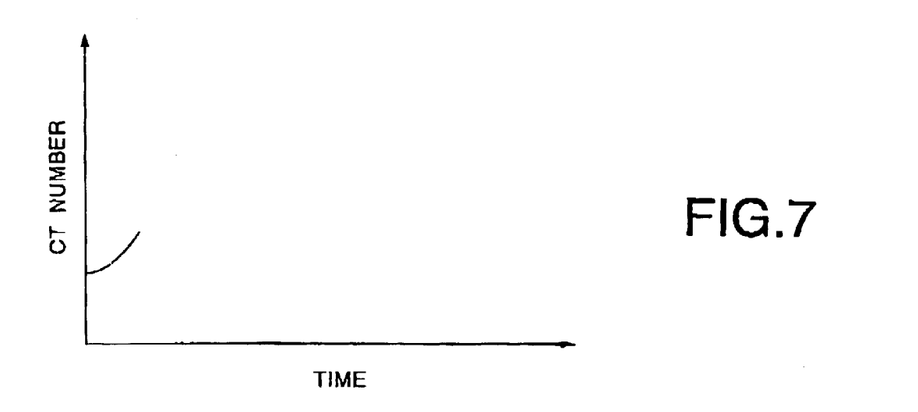
FIG. 7 is a chart showing a first exemplary aspect of transition of a contrast agent at a pre-scan position according to an embodiment of the present invention.

The image memory 16 stores the reconstructed data as the tomographies. The ROI setting unit 17 sets a region of interest (ROI) for the tomographies stored in the image memory 16. The ROI is an area determined to be focused in diagnosis. The CT number calculation unit 18 calculates a mean CT number in the ROI of each of the tomographies stored in the image memory 16. The chart preparation unit 19 produces and prepares a chart showing the CT numbers plotted along a time elapse updated as each of the CT numbers is calculated for each of the tomographies. The image memory 20 stores the chart. The adder 21 adds the chart stored in the image memory 20 to the tomographies stored in the image memory 16. The image display 22 displays the tomographies with the chart in its monitor. In fact, each tomography corresponding to each scanned slice is displayed with the chart in real time. The chart shows a CT number corresponding to the each tomography with the past CT numbers as shown in FIG. 7, for example.

Figure 2:
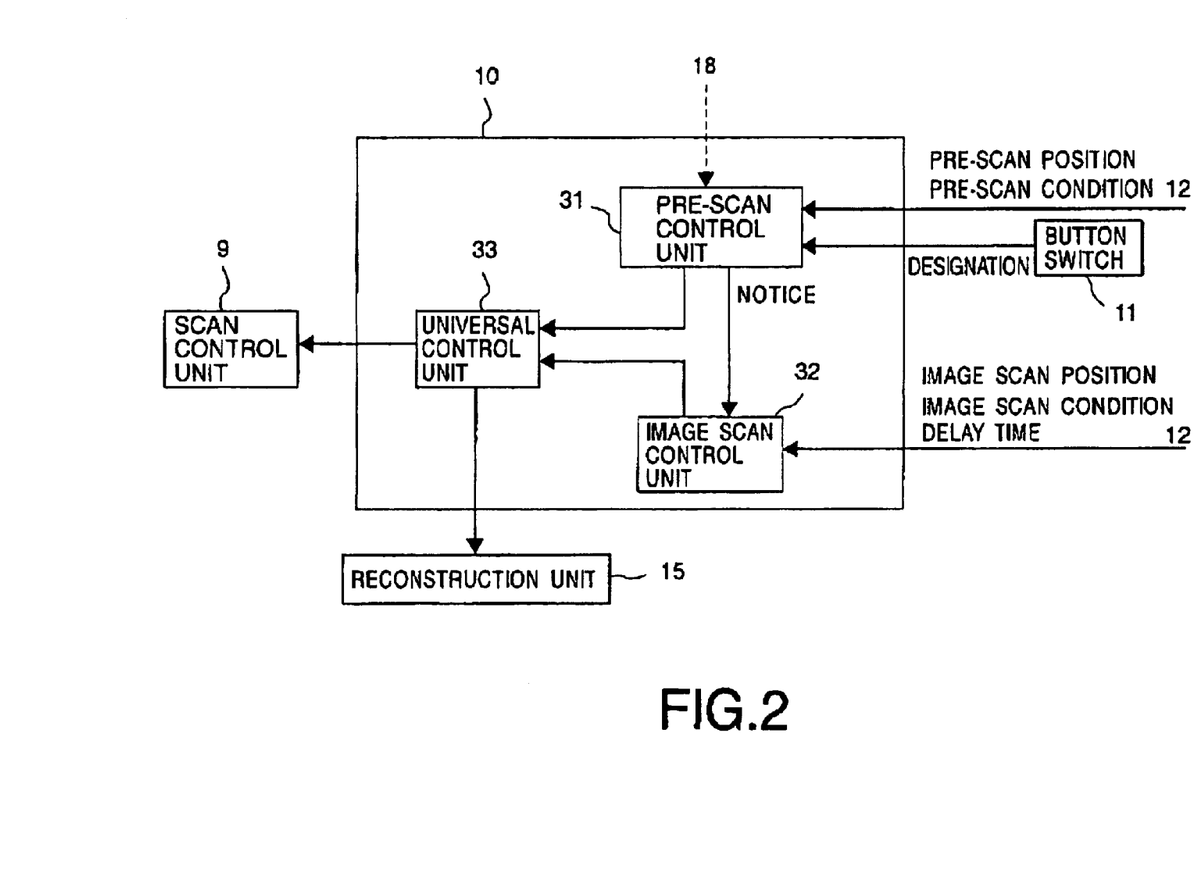
FIG. 2 is a diagram showing an exemplary configuration of a system control unit according to an embodiment of the present invention.

Next, the system control unit 10 is described in more detail with reference to FIG. 2. FIG. 2 is a diagram showing an exemplary configuration of the system control unit 10 according to an embodiment of the present invention. The system control unit 10 may include a pre-scan control unit 31, an image scan control unit 32, and a universal control unit 33. The pre-scan control unit 31 is connected with the button switch 11 and the operation panel 12. The pre-scan control unit 31 may also be connected with the CT number calculation unit 18. The image scan control unit 32 is connected with the operation panel 12.

The pre-scan control unit 31 receives the designation signal designating termination of the pre-scan from the button switch 11. The designation signal may be generated in response to a press of the button switch 11 by the operator. The pre-scan control unit 31 also receives the information input from the operation panel. 12. The information to be received by the pre-scan control unit 31 includes a position of the pre-scan and a condition of the pre-scan, such as, for example, an X-ray tube current, a slice thickness, and a scanning period, if necessary. The position and the condition received by the pre-scan control unit 31 are provided to the universal control unit 33 and further on to the gantry section 100. Accordingly the pre-scan will be implemented in accordance with the position and the condition.

Figure 6:
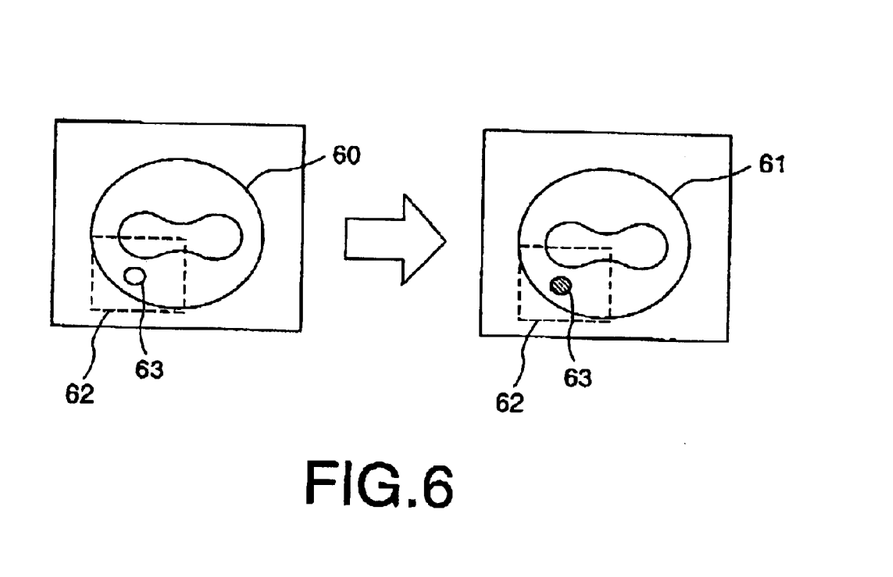
FIG. 6 is an illustration showing an example of displayed tomographies according to an embodiment of the present invention.

During the pre-scan, the operator observes the CT numbers in the chart and/or changing looks in the ROI of the tomographies displayed in the image display 22. When the operator determines that the CT number has reached a predetermined reference value or the contrast agent has reached enough to the slice position of the pre-scan, for example, as shown in FIG. 6, the operator may press the button switch 11. The button switch 11 generates the designation signal. Responsive to the designation signal, the pre-scan control unit 31 informs the universal control unit 33 of that the pre-scan should be terminated. Accordingly, the X-ray for the pre-scan is terminated in the X-ray tube 1. Further, the pre-scan control unit 31 provides the image scan control unit 32 with a notice of the pre-scan termination.

Instead of the designation signal from the button switch 11, which is manually operated, an alternative designation signal may be provided from the CT number calculation unit 18. If the CT number calculation unit 18 has a feature of determining whether the calculated CT number has reached the reference value or not and of giving a notice of such reaching to the pre-scan control unit 31, the pre-scan control unit 31 receives the notice as the alternative designation signal and acts in a similar manner to the above description. In such an automatic operation, it can be possible to avoid missing an appropriate timing for terminating the pre-scan and moving on to the image scan even if the operator accidentally failed to press the button switch 11 at the timing. In practice, it may be preferable to equip both the button switch 11 and the automatic notice feature so that one of these can be selected or both of these can be utilized together as the operator prefers.

Similar to the pre-scan control unit 31, the image scan control unit 32 receives the information input from the operation panel 12. The information to be received by the image scan control unit 32 includes a position of the image scan and a condition of the image scan. The position information may include an initial position of the image scan and an end position of the image scan. The condition information may include an X-ray tube current for the image scan, a slice thickness for the image scan, and the delay time. The position and the condition received by the image scan control unit 32 are provided to the universal control unit 33 and further on to the gantry section 100. Accordingly, the image scan will be ready for implementing in accordance with the position and the condition.

As explained before, the delay time is a time difference between the termination of the pre-scan and the initiation of the image scan. That is to say, the delay time indicates how long after the termination of the pre-scan the image scan should be initiated. The appropriate or desired delay time may be determined based on experiences of the operator. A period for the delay time may depend on the specimen P, an examining part of the body, a distance between the positions of the pre-scan and the image scan, or the like. After the delay time has elapsed from the time of the notice from the pre-scan control unit 31, the image scan control unit 32 informs the universal control unit 33 of that the image scan should be initiated. Accordingly, the image scan is initiated in the gantry section 100.

The universal control unit 33 is connected to the scan control unit 9 and to the reconstruction unit 15.

Figure 3:
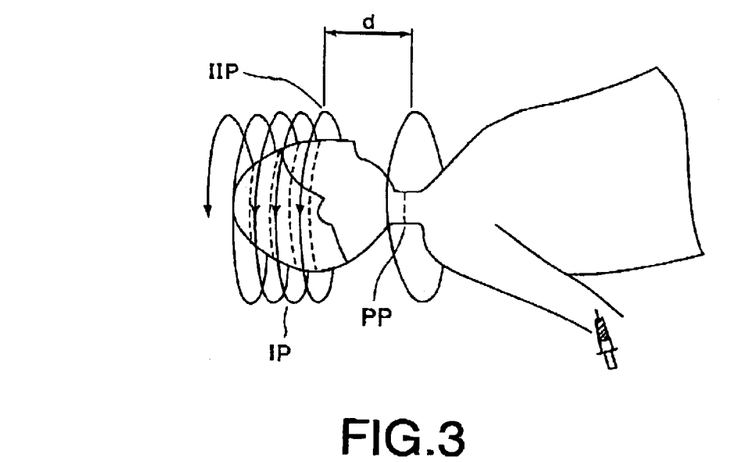
FIG. 3 is an illustration showing exemplary positions of a pre-scan and an image scan according to an embodiment of the present invention.

FIG 3 is an illustration showing exemplary positions of the pre-scan and the image scan according to an embodiment of the present invention. In FIG. 3, an exemplary pre-scan position PP is determined at a jugular of the specimen P. Further, an exemplary image scan position IP is determined at a head of the specimen P. As recognized in FIG. 3, the pre-scan position PP may be fixed at one position since the purpose of the pre-scan is to monitor whether the injected contrast agent has reached the pre-scan position or not, which is an indication that the contrast agent may soon be reaching the image scan position. In this example shown in FIG. 3, there is a distance d between the pre-scan position PP and an initial position IIP of the image scan. It may be usual to move the bed 4 towards the feet of the specimen P along the body axis with the distance d when the pre-scan has been terminated at the pre-scan position PP.

Figure 4:
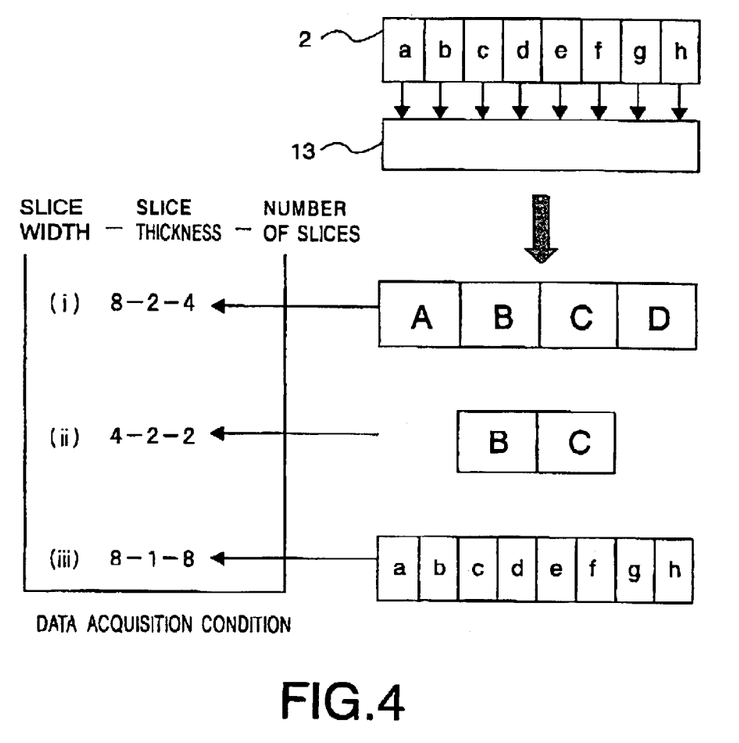
FIG. 4 is an illustration showing an example of data acquisition patterns according to an embodiment of the present invention.

FIG. 4 is an illustration showing an example of data acquisition patterns according to an embodiment of the present invention. The X-ray detector 2 comprises a plurality of detecting elements in two-dimensional direction as explained before The number of the detecting elements may depend on kinds of X-ray detectors. In FIG. 4, there are shown eight detecting elements a–h of the X-ray detector 2. This means that the X-ray detector 2 includes at least eight detecting elements a–h along the body axis. When the eight detecting elements a–h are ready for a use in detection, this is defined as a slice width with eight detecting elements. Detected data in the detecting elements a–h are acquired in the DAS unit 13. Switching by the analog switch provided between the X-ray detector 2 and the DAS unit 13, a result of the data acquisition may change as explained before.

In FIG. 4, when each two of the adjacent detecting elements, such as a detecting element a and a detecting element b, a detecting element c and a detecting element d, a detecting element e and a detecting element f, and a detecting element g and a detecting element h, are added (stacked) by the switching, the acquisition result comprises four segments A, B, C, and D (pattern (i)). Each segment uses detected data from each two detecting elements and has a slice thickness twice as wide as a width of one detecting element. One segment corresponds to one slice in the multi-slice scan. Therefore, in the pattern (i), the X-ray acquisition is made with the slice width of eight detecting elements. In the slice width, four slices are included, each of which has a slice thickness equivalent of two detecting elements.

In the pre-scan, the following pattern (ii) may be used. In the pattern (ii), only four detecting elements c–f are used for detection. When each two of adjacent detecting elements, such as a detecting element c and a detecting element d, and a detecting element e and a detecting element f, are added (stacked) by the switching, the acquisition result comprises two segments B and C. Each segment (slice) has a slice thickness twice as wide as the width of one detecting element. Therefore, in the pattern (ii), the X-ray acquisition is made with the slice width of four detecting elements. In the slice width, two slices are included, each of which has a slice thickness equivalent of two detecting elements. This is because the pre-scan does not require a wide range of scanning since it is only for monitoring arrival of the contrast agent. Further, it is important to avoid unnecessary X-ray exposure to the specimen P. Since the pre-scan is usually implemented with a lower intensity of an X-ray than the image scan, the addition (stack) of two detecting elements may be useful in the pre-scan in order to improve a quality of the tomographies displayed in the image display 22. Usually a monitored blood vessel in the ROI where the contrast agent flows with blood is very thin and so it may not be easy to recognize an appearance of the contrast agent if an image quality is inferior.

When it comes to the image scan, the following pattern (iii) may be applied. In the pattern (iii), since no addition (stack) of the detecting elements is made, the acquisition result comprises eight segments a to h. Each segment (slice) has the same slice thickness as the width of one detecting element. This makes it possible to scan a wide range in a single rotation scan which makes it shorter in time than when the scan is made in the condition of the pattern (ii). Scanning in a shorter time is helpful to reduce X-ray exposure to the specimen P. Therefore, in the pattern (iii), the X-ray acquisition is made with the slice width of eight detecting elements. In the slice width, eight slices are included, each of which has a slice thickness equivalent of one detecting element.

Figure 5:
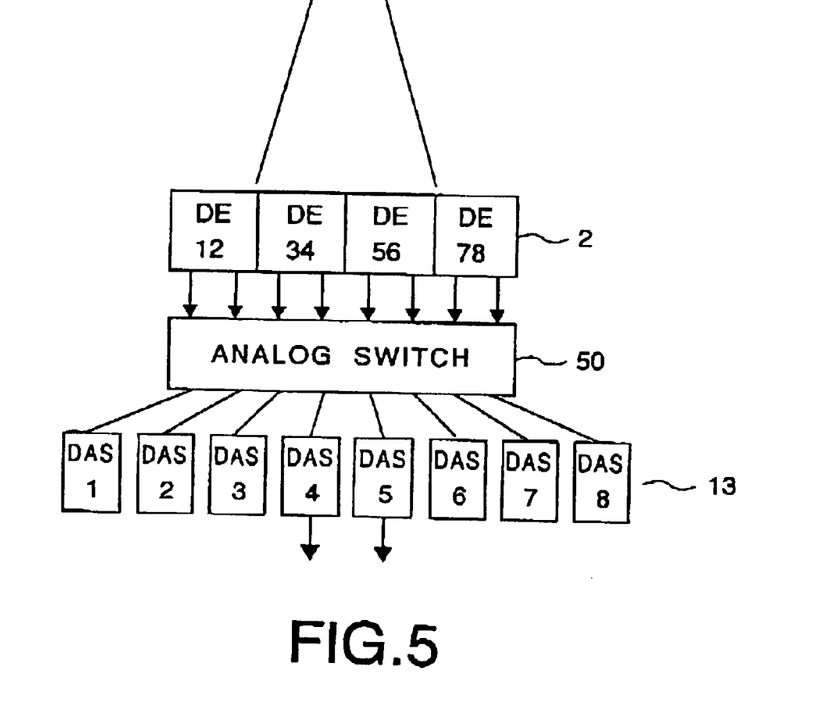
FIG. 5 is a block diagram showing a configuration regarding an X-ray detection and a data acquisition in the pre-scan according to an embodiment of the present invention.

The pre-scan in the above pattern (ii) will be described in more details with reference to FIG. 5. FIG. 5 is a block diagram showing a configuration regarding an X-ray detection and a data acquisition in the pre-scan according to an embodiment of the present invention. In order to have a clear image for the slice thickness equivalent of a width resulting from a stack of the two detecting elements, the X-ray detector 2 is visualized as including four detecting segments DE12, DE34, DE56, and DE78. For example, the detecting segment DE34 means a stack of detecting elements DE3 and DE4. As explained in FIG. 4, the pre-scan is implemented in two-slice scan while the X-ray tube 1 radiates an X-ray so that a transmission X-ray transmitted from the specimen P resulting from the X-ray by the X-ray tube 1 is exposed to two detecting segments DE34 and DE56. Therefore, for example, the detecting segment DE34 may correspond to a first slice and the detecting segment DE56 may correspond to a second slice. In other words, a first transmission X-ray transmitted from a first part of the specimen P regarding the first slice in the pre-scan may be detected in the detecting segment DE34, Similarly, a second transmission X-ray transmitted from a second part of the specimen P regarding the second slice in the pre-scan may be detected in the detecting segment DE56.

X-ray data detected by the detecting segments DE34 and DE56 are supplied to the DAS unit 13 through an analog switch 50. The analog switch 50 is provided in between the X-ray detector 2 and the DAS unit 13 and switches the connection or the relationship between detecting elements DE1 to DE8 and DAS elements DAS1 to DAS8. In FIG. 5, for example, the detecting elements DE3 and DE4 included in the detecting segment DE34 may be connected to the DAS element DAS4 by the analog switch 50. Similarly, for example, the detecting elements DE5 and DE6 included in the detecting segment DE56 may be connected to the DAS element DAS5 by the analog switch 50. The DAS element DAS4 acquires data detected by the detecting elements DE3 and DE4 and supplies acquired data to the reconstruction unit 15 for the image reconstruction processing through the memory 14. Similarly, the DAS element DAS5 acquires data detected by the detecting elements DE5 and DE6 and supplies acquired data to the reconstruction unit 15 for the image reconstruction processing through the memory 14. The other DAS elements DAS1, DAS2, DAS3, DAS6, DAS7, and DAS8 may or may not be supplied data which are not based on the X-ray radiation by the X-ray tube 1. Such supplied data may not be supplied to the reconstruction unit 15.

Once the pre-scan is initiated with the X-ray detector 2, the analog switch 50, and the DAS unit 13 in the condition described above, the operator begins to observe tomographies displayed in the image display 22. In the observation, the operator concentrates on the ROI set in advance. FIG. 6 is an illustration showing an example of displayed tomographies according to an embodiment of the present invention. Immediately after the initiation of the pre-scan, the image display 22 displays a tomography 60. In the tomography 60, there is set an ROI 62 including the carotid artery 63 as shown in the left side of FIG. 6. Since it is an initial stage, the contrast agent injected to the specimen P has not arrived yet at the carotid artery 63 at the pre-scan slice position. Therefore, the contrast agent is not appearing in the carotid artery 63 in the displayed tomography 60 yet. Contrary to the initial stage, in a predetermined time after the initial stage, a tomography 61 may be displayed in the image display 22. As a result of elapse of the predetermined time, the contrast agent injected to the specimen P has arrived at the carotid artery 63 at the pre-scan slice position. Therefore, the contrast agent is observed in the carotid artery 63 in the tomography 61. In the image display 22, every tomography during the pre-scan is continuously displayed in a manner similar to a cine-mode display, which is like a moving picture.

When the tomographies such as those shown in FIG. 6 are displayed, a chart showing CT numbers may be displayed together with the tomographies, too. The tomographies and the chart may alternatively be switched each other and displayed independently.

Figure 8:
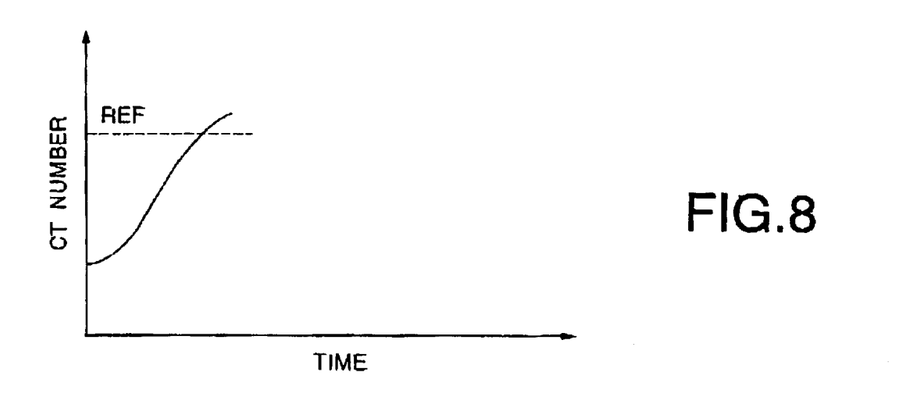
FIG. 8 is a chart showing a second exemplary aspect of transition of the contrast agent at the pre-scan position according to an embodiment of the present invention.
Figure 9:
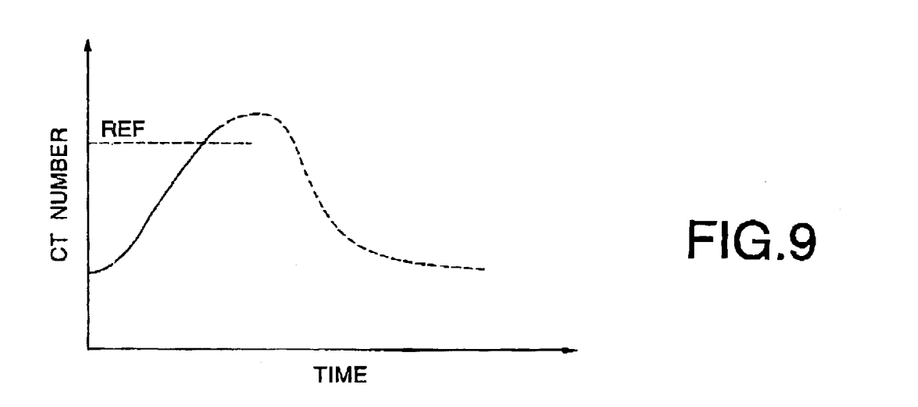
FIG. 9 is a chart showing a third exemplary aspect of transition of the contrast agent at the pre-scan position according to an embodiment of the present invention.

FIGS. 7 to 9 are charts showing exemplary aspects of transition of the contrast agent at the pre-scan position according to an embodiment of the present invention. As explained above, the contrast agent is not appearing in the carotid artery at the pre-scan slice position at the very initial stage. Afterwards, as time goes by, the contrast agent begins to reach the pre-scan slice position little by little. One aspect in such a stage is recognized in a chart showing transition of CT numbers in the ROI of tomographies at the pre-scan slice position as shown in FIG. 7. Since the pre-scan is initiated a little after the contrast agent injection, the CT numbers obtained based on the tomographies in the pre-scan has already started to increase slowly. Further later on, the CT numbers increase more, and reach the predetermined reference value as shown in FIG. 8 while a tomography displayed in the image display 22 at this stage may look like the tomography 61 already shown in FIG. 6. It would be useful to set such a predetermined reference value for the CT number in the event that the pre-scan is set to be automatically terminated. Even if not, it may still be helpful to set the predetermined reference value since it could help the operator to judge the timing to terminate the pre-scan. If the pre-scan continued at the pre-scan slice position, the transition of the CT numbers might be tracked as shown in FIG. 9. After the CT number has reached a peak level, it goes down to, the level equivalent of that at the initial stage as the contrast agent passes and runs off the pre-scan slice position.

Responsive to the termination of the pre-scan, the bed 2 or perhaps a set of the X-ray tube 1 and the X-ray detector 2 is moved to the position where the image scan is initiated. When the scan position is changed, the slice width of the X-ray detector 2 is also changed wider as shown in FIG. 10.

Figure 10:
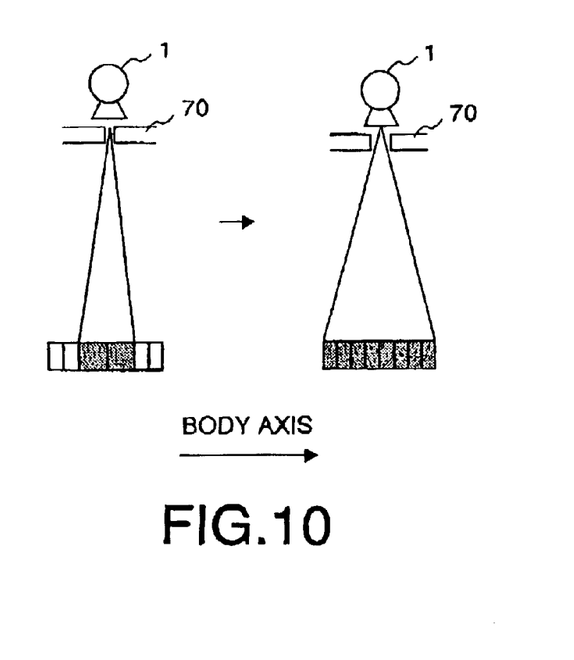
FIG. 10 is an illustration showing an example of an X-ray exposure width change of an X-ray detector according to an embodiment of the present invention.

FIG. 10 is an illustration showing an example of an X-ray exposure width change of the X-ray detector 2 according to an embodiment of the present invention. As explained in FIGS. 4 and 5, the pre-scan is implemented with a narrower first slice width than the image scan and may, for example, be implemented with the first slice width equivalent of a width of four detecting elements. A collimator 70 collimates the X-ray radiated from the X-ray tube 1 so that a collimated X-ray is exposed to a width corresponding to the first slice width of the X-ray detector 2. Further, the slice thickness may be equivalent of a width of two detecting elements. This is recognized in the left of FIG. 10. On the other hand, the image scan can be recognized in the right of FIG. 10. In the image scan, compared to the pre-scan, a second slice width may be set to the equivalence of eight detecting elements as explained as the pattern (iii) in FIG. 4. The collimator 70 collimates the X-ray radiated from the X-ray tube 1 with a wider aperture than in the pre-scan so that a collimated X-ray is exposed to a width corresponding to the second slice width of the X-ray detector 2. Further, the slice thickness may be equivalent of the width of one detecting element.

Figure 11:
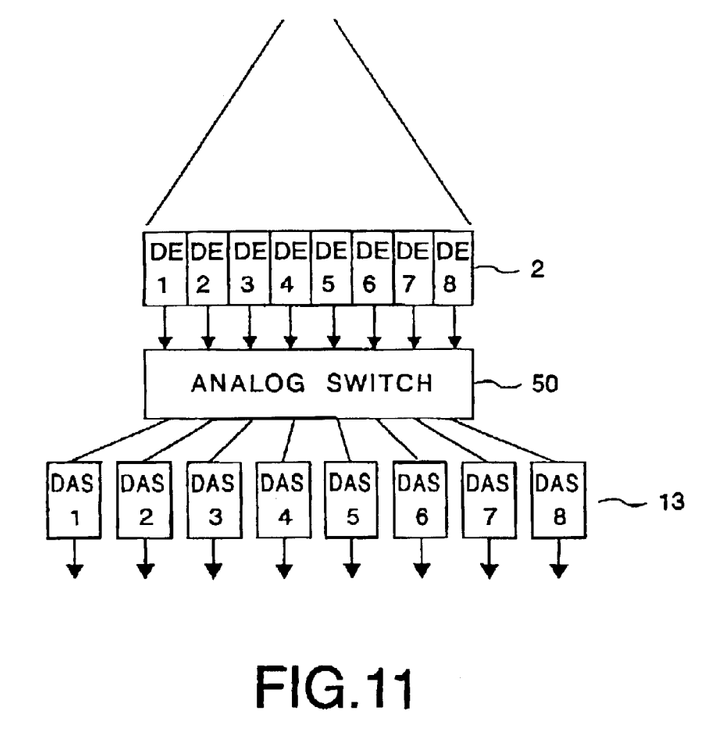
FIG. 11 is a block diagram showing a configuration regarding an X-ray detection and a data acquisition in the image scan according to an embodiment of the present invention.

Regarding the pre-scan, the exemplary connection between the X-ray detector 2 and the DAS unit 13 was described with reference to FIG. 5. In a similar fashion, an exemplary connection between the X-ray detector 2 and the DAS unit 13 regarding the image scan will be described with reference to FIG. 11. FIG. 11 is a block diagram showing a configuration regarding an X-ray detection and a data acquisition in the image scan according to an embodiment of the present invention.

The X-ray detector 2 may include detecting elements DE1 to DE8 as similar to FIG. 5. Here, however, each detecting element may be used for each slice as one detecting segment. The image scan is implemented in eight-slice scan while the X-ray tube 1 radiates an X-ray so that a transmission X-ray transmitted from the specimen P resulting from the X-ray by the X-ray tube 1 is exposed to eight detecting elements (segments) DE1 to DE8. Therefore, for example, the detecting elements DE1 to DE8 may correspond to a first slice to a eighth slice. In other words, a first transmission X-ray transmitted from a first part of the specimen P regarding the first slice in the image scan may be detected in the detecting element DE1. Similarly, a second transmission X-ray transmitted from a second part of the specimen P regarding the second slice in the image scan may be detected in the detecting element DE2. Further, a similar manner may be applied to the detecting elements DE3 to DE8.

X-ray data detected by the detecting elements DE1 to DE8 are supplied to the DAS unit 13 through the analog switch 50. The analog switch 50 is provided in between the X-ray detector 2 and the DAS unit 13 and switches the connection or the relationship between the detecting elements DE1 to DES and the DAS elements DAS1 to DAS8. As a preparation for the switching from the pre-scum to the image scan, the analog switch 50 needs to switch the previous connection made for the pre-scan to a connection for the image scan. This is because, for example, the detecting elements DE3 and DE4 were stacked and their output data were supplied to the DAS element DAS4 in the pre-scan. In FIG. 10, instead, the detecting elements DE1 to DE8 may be connected to the DAS elements DAS1 to DAS8, respectively, by the analog switch 50. The DAS element DAS1 acquires data detected by the detecting element DE1 and supplies acquired data to the reconstruction unit 15 for the image reconstruction processing through the memory 14. Similarly, the DAS elements DAS2 to DAS8 acquire data detected by the detecting elements DE2 to DE8, respectively, and supply acquired data to the reconstruction unit 15 for the image reconstruction processing through the memory 14.

With the above condition, the image scan will be initiated in the predetermined delay time after the termination of the pre-scan. When, however, the analog switch 50 has been changed and accordingly the connection status has been changed in between the detecting elements DE1 to DE8 and the DAS elements DAS1 to DAS8, an offset correction may be required for avoiding appearance of undesired noises in tomographies due to the connection change. For the offset correction, it is necessary for the X-ray detector 2 to detect data without an X-ray radiation by the X-ray tube 1. The data detected by the X-ray detector 2 is acquired by the DAS unit 13, and the offset correction is made based on the data acquired by the DAS unit 13. Since there tends to be a time-dependent fluctuation in the offset even if stacks between the detecting elements (a connection between the detecting elements and the DAS elements) are made in a similar fashion, it is not so effective to perform the offset correction in advance of the pre-scan, but rather immediately before the image scan. Therefore, in practice, it may be preferable to initiate the image scan after the offset correction.

Even with the offset correction, it may be possible to reduce an X-ray exposure to the specimen P according to an embodiment of the present invention since the pre-scan is implemented in a narrower slice width than in the image scan.

In the above case with the offset correction, a required time for the correction may not be so long. In fact, it is supposed to take only a little time (e.g. 0.5 sec) to make the offset correction. Ideally speaking, however, it is not desirable for the image scan to be accompanied by the pre-scan, which requires an extra time, besides the image scan time, and also causes an extra X-ray exposure to the specimen P in addition to the exposure necessary for the image scan. From this point of view, even such a little time for the offset correction may not be preferable. A reduction of time between the pre-scan and the image scan will be described with reference to FIGS. 12 and 13 according to an embodiment of the present invention.

Figure 12:
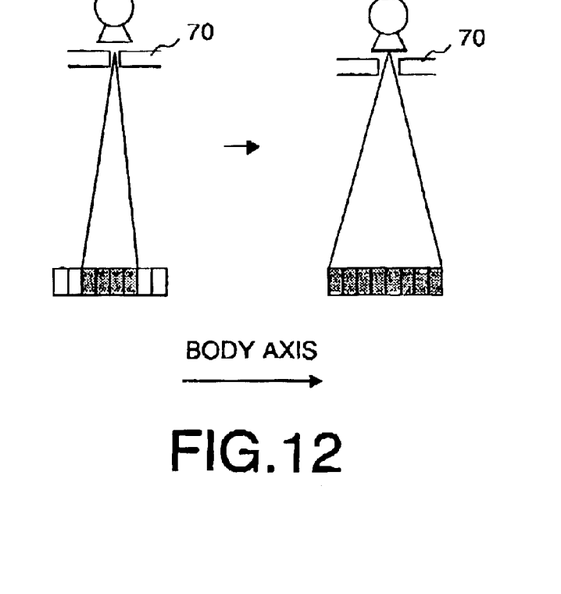
FIG. 12 is an illustration showing another example of an X-ray exposure width change of the X-ray detector according to an embodiment of the present invention.

FIG. 12 is an illustration showing another example of an X-ray exposure width change of the X-ray detector 2 according to an embodiment of the present invention. As shown in FIG. 12, the pre-scan is implemented with a first exposure width, which comprises four detecting segments. The first exposure width is the same width as the first slice width in the pre-scan shown in FIG. 10. Each of the detecting segments has a slice thickness equivalent of a width of one detecting element. The X-ray radiated from the X-ray tube 1 is collimated by the collimator 70 so that a collimated X-ray is exposed to the first exposure width of the X-ray detector 2. This is recognized in the left of FIG. 12. On the other hand, in the image scan, an exposure width (a second exposure width) and a slice thickness are the same as the second slice width and the slice thickness in the image scan explained in FIG. 10. This is recognized in the right of FIG. 12.

Figure 13:
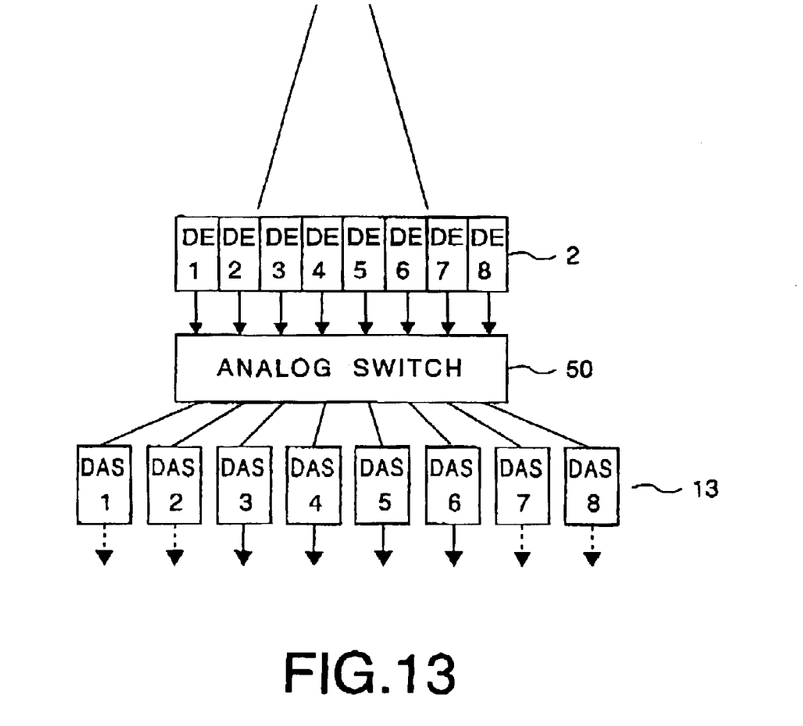
FIG. 13 is a block diagram showing another configuration regarding the X-ray detection and the data acquisition in the pre-scan according to an embodiment of the present invention.

FIG. 13 is a block diagram showing another configuration regarding the X-ray detection and the data acquisition in the pre-scan according to an embodiment of the present invention.

The X-ray detector 2 may include detecting elements DE1 to DE8 as similar to FIGS. 5 and 11. Here, each detecting element may be used for each slice as one detecting segment, not like in FIG. 5 for the pre-scan but similar to FIG. 11 for the image scan. The pre-scan is implemented in an eight-slice scan while the X-ray tube 1 radiates an X-ray which is collimated by the collimator 70 with an aperture similar to FIG. 5 so that a transmission X-ray transmitted from the specimen P resulting from the X-ray by the X-ray tube 1 is exposed to only four detecting elements (segments), such as, for example, the detecting elements DE3 to DE6. Therefore, the detecting elements DE1 to DE8 may correspond to a first slice to an eighth slice. Substantively, however, the detecting elements DE1, DE2, DE7, and DE8 are not material since these detecting elements are not exposed to the X-ray in substance, and a first transmission X-ray transmitted from a first part of the specimen P in the pre-scan may be detected in the detecting element DE3. Similarly, a second transmission X-ray transmitted from a second part of the specimen P in the pre-scan may be detected in the detecting element DE4. Further, a similar manner may be applied to the detecting elements DE5 and DE6.

X-ray data detected by the detecting elements DE1 to DE8 are supplied to the DAS unit 13 through the analog switch 50. The analog switch 50 provided in between the X-ray detector 2 and the DAS unit 13 switches the connection or the relationship between detecting elements DE1 to DE8 and the DAS elements DAS1 to DAS8. Here, the detecting elements DE 1 to DE8 are connected to the DAS elements DAS1 to DAS8, respectively, by the analog switch 50. The DAS element DAS1 acquires data from the detecting element DE1 and supplies acquired data to the reconstruction unit 15 through the memory 14. Similarly, the DAS elements DAS2 to DAS8 acquire data from the detecting elements 2 to 8, respectively, and supply acquired data to the reconstruction unit 16 through the memory 14. In the reconstruction unit 15, the data supplied from the DAS elements DAS1, DAS2, DAS7, and DAS8 are not used for the reconstruction processing. This is because the DAS elements DAS1, DAS2, DAS7, and DAS8 have acquired data from the detecting elements DE1, DE2, DE7, and DE8 where the X-ray has not intentionally been exposed. The reconstruction unit 15 reconstructs tomographies with the data supplied from the DAS elements DAS3 to DAS6.

Alternatively, the DAS element DAS1 acquires data from the detecting element DE1, but such acquired data may not be supplied to the reconstruction unit 15 in the end. Similarly, the DAS elements DAS2, DAS7, and DAS8 acquire data from the detecting elements 2, 7, and 8, respectively, but those acquired data may not be supplied to the reconstruction unit 15 in the end. Accordingly, the reconstruction unit 15 reconstructs the tomographies based on the data supplied from the DAS unit 13 (the DAS elements DAS3 to DAS6).

This condition shows that the X-ray detector 2 is exposed to the X-ray in the first exposure width but a slice width in this pre-scan is equivalent of a width of eight detecting elements.

After the reconstruction processing, image stacks may be implemented by a time of a display in the image display 22. In the image stacks, first image data reconstructed based on the data supplied from the DAS element DAS3 and second image data reconstructed based on the data supplied from the DAS element DAS4 are stacked as first tomography data. Similarly, third image data reconstructed based on the data supplied from the DAS element DAS5 and fourth image data reconstructed based on the data supplied from the DAS element DAS6 are stacked as second tomography data. Accordingly, tomographies based on the first and second tomography data are displayed in the image display 22. The displayed tomographies may have an image quality similar to that of tomographies displayed based on the data detection and acquisition in FIG. 5.

According to an embodiment of the present invention, data stacks may not be limited to the way described above. As one of alternative examples, raw data stacks may be applicable regardless whether the data acquired in the DAS elements DAS1, DAS2, DAS7, and DAS8 are supplied to but not used in the reconstruction unit 15 or not supplied. In the alternative way, the data acquired in the DAS elements DAS3 and DAS4 are stacked as one data (first raw data) before the reconstruction processing in the reconstruction unit 15. Similarly, the data acquired in the DAS elements DAS5 and DAS6 are stacked as one data (second raw data) before the reconstruction processing in the reconstruction unit 15. Accordingly, the reconstruction unit 16 reconstructs tomographies based on the first raw data and the second raw data, respectively. Reconstructed tomographies are displayed as tomographies in the image display 22. According to the raw data stacks, the data stacks are implemented with a use of raw data of before the reconstruction processing. Therefore, the displayed tomographies may have an image quality similar to or rather better than that of tomographies displayed based on the image data stacks described before.

After the pre scan with the condition described above, the image scan will be followed. As shown in FIG. 13, the slice width and the slice thickness in the pre-scan are the same as those shown in FIG. 11. This indicates that there is no necessity of changing the connection between the detecting elements DE1 to DE8 and the DAS elements DAS1 to DAS 8 by the analog switch 50. Therefore, without making the offset correction, the image scan will be initiated in a predetermined delay time after the termination of the pre-scan. This contributes to a reduction of an examination time.

Figure 14:
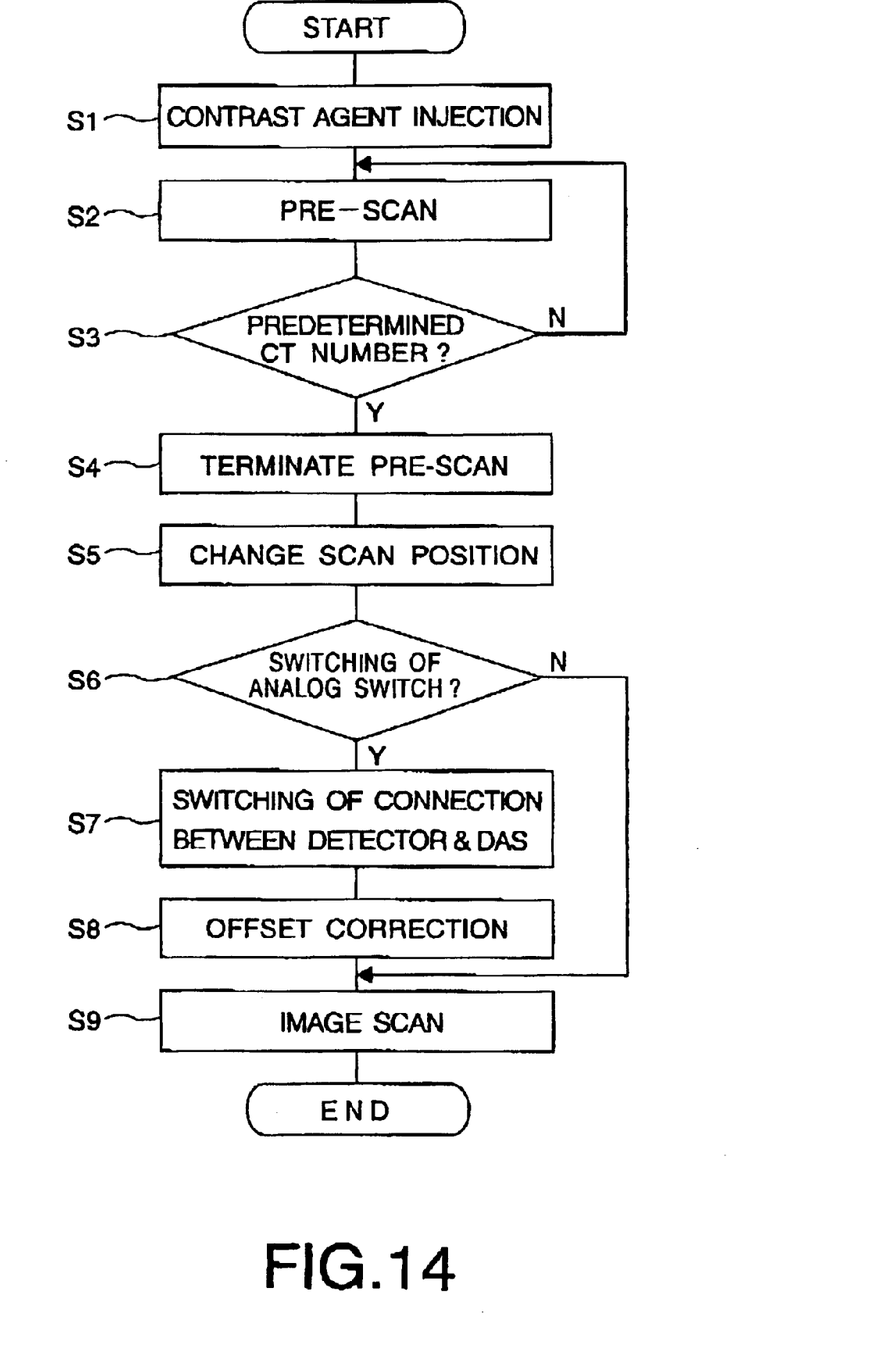
FIG. 14 is a flowchart showing an exemplary examination procedure in the CT apparatus according to an embodiment of the present invention.

Next, an operation of the CT apparatus will be explained with reference to FIG. 14 when the CT apparatus is configured as described above. FIG. 14 is a flowchart showing an exemplary examination procedure in the CT apparatus according to an embodiment of the present invention.

In FIG. 14, an examination with a contrast agent will be taken as an example of the examination procedure. First of all, the contrast agent is injected to the specimen P so as to enhance a particular part of his or her body in tomographies obtained by the CT apparatus (step S1). Immediately after the injection in step S1, the pre-scan is initiated with an X-ray exposed to a first width of the X-ray detector 2 (e.g. to four detecting elements) along the body axis (step S2). The pre-scan may be fixed and performed at the first position of the specimen P with an X-ray intensity lower than that for a coming image scan. The first position may be adjacent to the second position where the image scan is initiated. During the pre-scan, tomographies obtained may be displayed sequentially and substantially in real time in the image display 22. In addition, a chart showing CT numbers is displayed in the image display 22, too. The CT numbers correspond to the images displayed together. The operator observes the images and the CT numbers. During the observation, it is determined whether at least one of the CT numbers has reached or exceeded a predetermined reference value (step S3). The pre-scan is not terminated until that the at least one CT number has reached or exceeded the predetermined reference value. When a CT number corresponding to an image at a time reaches or exceeds the predetermined reference value, the pre-scan is terminated (step S4). The termination may be automatically controlled by the system control unit 10. Alternatively, the operator may terminate the pre-scan by operating the button switch 11.

Responsive to the termination of the pre-scan, the scan position is changed to the second position (step S5). For initiating the image scan, it is determined whether it is necessary for the analog switch 50 to change its switching c(r not (step S6). If the connection between the detecting elements and the DAS elements are identical in between the pre-scan and the image scan, (in other words, if a predetermined slice width and a predetermined slice thickness are used in common in between the pre-scan and the image scan), the analog switch 50 is not required to switch and change the connection. If, however, at least one of a slice width and a slice thickness is different in between the pre-scan and the image scan, the analog switch 50 switches the connection between the detecting elements and the DAS elements (step S7). Following the connection switching by the analog switch 50, the offset correction may be made without radiation by the X-ray tube 1 (step S8).

After completing the offset correction, the CT apparatus begins to implement the image scan (step S9). The image scan is initiated at the second position with an X-ray intensity required for the imaging. The required intensity may be higher than that in the pre-scan. The image scan may be performed in a helical (or spiral) manner. A set of the X-ray tube 1 and the X-ray detector 2 may continue to rotate around the specimen P from the initiation of the pre-scan until the termination of the image scan. When the image scan has been completed over a predetermined scanning range of the specimen P, the image scan is terminated.

Although the flowchart shown in FIG. 14 has been explained above, the procedure flow of the CT apparatus according to embodiments of the present invention is not limited to the above description made for FIG 14. Any explanation made in the embodiments described above can be applied to any applicable process as appropriately.

Further, the pre-scan is not limited to a two-slice scan or a four-slice scan described above. Any number of slice scan, including a single slice scan, may be applied to the pre-scan as appropriately in accordance with an examination situation, according to embodiments of the present invention.

Still further, in the embodiments of the present invention, the CT apparatus may have a random access memory (RAM), which can receive and store computer programs and applications as computer readable instructions in a temporary and/or non-volatile state. The CT apparatus may further have a hard disk drive as part of the controller for reading from and writing to a hard disk, a magnetic disk drive for reading from and writing to a magnetic disk, and/or an optical disk drive for reading from and writing to an optical disk (such as a CD, CDR, CD-RW, DVD, or other optical device). Those skilled in the art will appreciate that one or more of such memory, drives, and their respective media are examples of a computer program product for storing computer readable instructions, which when executed, may implement an embodiment of the present invention.

Accordingly, a CT apparatus which does not incorporate features of embodiments of the present invention can benefit the features as long as the CT apparatus is equipped with a feature of a multi-slice scan and a real time scan as well as a feature of reading and performing a computer readable program.

The embodiments of the present invention described above are examples described only for making it easier to understand the present invention, and are not described for the limitation of the present invention. Consequently, each component and element disclosed in the embodiments of the present invention may be redesigned or modified to its equivalent within a scope of the present invention. Furthermore, any possible combination of such components and elements may be included in a scope of the present invention as long as an advantage similar to those obtained according to the above embodiments of the present invention is obtained.

What is claimed is:

1. An X-ray computed tomography apparatus, comprising:
    an X-ray generator configured to generate a first X-ray in a pre-scan mode and a second X-ray in an image scan mode;
    an X-ray detector configured to detect a first transmission X-ray exposed through a specimen to a first exposure width of the X-ray detector along a body axis of the specimen, resulting from the first X-ray at a first scanning position in the pre-scan mode and to detect a second transmission X-ray exposed through the specimen to a second exposure width of the X-ray detector along the body axis of the specimen, resulting from the second X-ray at a second scanning position in the image scan mode, the first exposure width being narrower than the second exposure width;
    a controller configured to control the first scanning position and the second scanning position; and
    a display configured to display a first image based on the first transmission X-ray detected by the X-ray detector and a second image based on the second transmission X-ray detected by the X-ray detector.

2. The apparatus according to claim 1, further comprising a collimator, provided in between the X-ray generator and the X-ray detector, configured to collimate the first X-ray and the second X-ray, and wherein the controller is further configured to control the collimator to change a collimating width so that the fist transmission X-ray and the second transmission X-ray are exposed to the first exposure width and the second exposure width of the X-ray detector, respectively.

3. The apparatus according to claim 1, wherein the controller is further configured to control the X-ray generator to change a generation angle along the body axis so that the first transmission X-ray and the second transmission X-ray are exposed to the first exposure width and the second exposure width of the X-ray detector, respectively.

4. The apparatus according to claim 1, wherein, when a distance between the X-ray generator and the X-ray detector is variable, the first transmission X-ray is exposed to the first exposure width of the X-ray detector when the distance is a first distance and the second transmission X-ray is exposed to the second exposure width of the X-ray detector when the distance is a second distance longer than the first distance.

5. The apparatus according to claim 1, wherein an intensity of the first X-ray is lower than an intensity of the second X-ray.

6. The apparatus according to claim 1, wherein a number of slices in a single scan in the pre-scan mode is smaller than a number of slices in a single scan in the image scan mode.

7. The apparatus according to claim 1, wherein the X-ray detector comprises a plurality of detecting elements along the body axis; and wherein each scanning slice in the pre-scan mode uses at least two of the plurality of detecting elements.

8. The apparatus according to claim 1, wherein the X-ray detector comprises a plurality of detecting elements along the body axis; and wherein the first exposure width is over a first number of the plurality of detecting elements along the body axis and the second exposure width is over a second number of the plurality of detecting elements along the body axis, the first number being smaller than the second number.

9. The apparatus according to claim 8, further comprising a data acquisition unit, comprising a plurality of data acquisition elements, configured to acquire data output from the X-ray detector; and a switch configured to switch a connection between the plurality of detecting elements and the plurality data acquisition elements, and wherein the connection is kept identical in between the pre-scan mode and the image scan mode.

10. The apparatus according to claim 1, further comprising a data acquisition unit, comprising a plurality of data acquisition elements, configured to acquire data output from the X-ray detector, and wherein a predetermined number of the data acquisition elements are commonly used in both the pre-scan mode and the image scan mode.

11. The apparatus according to claim 10, further comprising a reconstruction unit configured to reconstruct an image based on at least a portion of the data acquired by the data acquisition unit, and wherein a remaining portion of the data acquired by the data acquisition unit is not used for reconstruction by the reconstruction unit in the pre-scan mode.

12. The apparatus according to claim 1, wherein the first scanning position is fixed along the body axis.

13. The apparatus according to claim 1, wherein the second scanning position is movable along the body axis.

14. The apparatus according to claim 1, wherein the second scanning position is achieved by moving at least the X-ray generator and the X-ray detector from the first scanning position relative to the body axis in response to an manual designation by an operator.

15. The apparatus according to claim 1, wherein the second scanning position is achieved by moving at least the X-ray generator and the X-ray detector from the first scanning position relative to the body axis in response to that a CT number of the first image has reached a predetermined reference value.

16. The apparatus according to claim 1, further comprising a calculator configured to calculate a CT number in a predetermined region of the first image, and wherein a scan in the pre-scan mode is automatically terminated when the specimen is injected with a contrast agent and the CT number calculated by the calculator has reached a predetermined reference value.

17. The apparatus according to claim 16, wherein the controller is further configured to change the first scanning position to the second scanning position, responsive to termination of the scan in the pre-scan mode; and wherein a scan in the image scan mode is initiated at the second scanning position in a predetermined time after the termination of the scan in the pre-scan mode.

18. The apparatus according to claim 1, wherein the display is further configured to display a CT number in a predetermined region of the first image in the pre-scan mode.

19. The apparatus according to claim 1, wherein the X-ray detector comprises a plurality of detecting elements along the body axis; and wherein first data based on detection by one of the plurality of detecting elements under the first exposure width are stacked with second data based on detection by at least one other of the plurality of the detecting elements under the first exposure width in the pre-scan mode.

20. The apparatus according to claim 19, further comprising a reconstruction unit configured to reconstruct an image based on third data resulting from the stack of the first data and the second data, and wherein the data stacking in the pre-scan mode is performed before the first data and the second data are supplied to the reconstruction unit.

21. The apparatus according to claim 1, further comprising a data acquisition unit, comprising a plurality of data acquisition elements, configured to acquire data output from the X-ray detector, and wherein the X-ray detector comprises a plurality of detecting elements along the body axis; and wherein at least one of the detecting elements to be used, a slice thickness to be used in a single slice, and at least one of the data acquisition elements to be used are common between the pre-scan mode and the image scan mode.

22. The apparatus according to claim 1, wherein a number of slices in a single scan in the pre-scan mode is smaller than a number of slices in a single scan in the image scan mode according to a difference between the first exposure width and the second exposure width.

23. The apparatus according to claim 1, wherein the X-ray detector comprises a plurality of detecting elements along the body axis; and wherein a number of the detecting elements to be used in the pre-scan mode is smaller than another number of the detecting elements to be used in the image scan mode according to a difference between the first exposure width and the second exposure width.

24. The apparatus according to claim 1, further comprising a data acquisition unit, comprising a plurality of data acquisition elements, configured to acquire data output from the X-ray detector, and wherein the X-ray detector comprises a plurality of detecting elements along the body axis; and wherein each of the plurality of data acquisition elements acquires the data output from one or more of the plurality of detecting elements.

25. The apparatus according to claim 1, further comprising a data acquisition unit, comprising a plurality of data acquisition elements configured to acquire data output front the X-ray detector; and a reconstruction unit configured to reconstruct an image based on the data output acquired by the data acquisition unit; wherein the X-ray detector comprises a plurality of detecting elements along the body axis; and wherein information from one or more of the data acquisition elements not corresponding to detecting elements under the first exposure width is not used as the data output for reconstruction of the image by the reconstruction unit in the pre-scan mode.

26. The apparatus according to claim 1, further comprising an input device configured to input information regarding determining an image scan condition for the image scan mode; and wherein the controller is further configured to determine the image scan condition for the image scan mode based on the information and also to automatically determine a pre-scan condition for the pre-scan mode based on the determined image scan condition.

27. The apparatus according to claim 26, wherein, when a plurality of predetermined pre-scan conditions are prepared, each of which corresponding to each of a plurality of parts of the specimen, for the image scan condition, the controller determines one of the plurality of predetermined pre-scan conditions, as a determined pre-scan condition, which corresponds to one of the plurality of parts indicated in the determined image scan condition.

28. The apparatus according to claim 1, further comprising a reconstruction unit configured to reconstruct an image based on data resulting from detection by the X-ray detector, and wherein the reconstruction unit performs reconstruction in a real time reconstruction manner in the pre-scan mode.

29. An X-ray computed tomography apparatus, comprising;
an X-ray source configured to radiate an X-ray to a specimen;
a collimator configured to vary a collimating width, along a body axis of the specimen, which determines an X-ray width exposed to the specimen;
a detector, comprising a plurality of detecting elements along the body axis, configured to detect a transmission X-ray transmitted from the specimen;
a data acquisition unit, comprising a plurality of data acquisition elements along the body axis, configured to acquire data output from the detector;
is an implementing unit configured to implement a scan around the specimen with the X-ray source and the X-ray detector;
a controller configured to control a scan mode to switch from a pre-scan to an image scan, and to control the collimator to make the collimating width wider in the image scan than in the pre-scan, the pre-scan being for monitoring a CT number in a predetermined region of interest of the specimen, the image scan being for scanning an examining region of the specimen; and
a reconstruction unit configured to reconstruct a tomography of the specimen based on the data output acquired in the pre-scan, and also to reconstruct an image of the specimen based on projection data acquired in the image scan.

30. The apparatus according to claim 29, further comprising a switch configured to switch a number of the data acquisition elements to be used; and wherein the controller is further configured to control the switch so that the number of the data acquisition elements to be used is identical in both the pre-scan and the image scan.

31. The apparatus according to claim 29, further comprising:
a setting unit, when a plurality of slices are obtained in each single rotation of the scanning, configured to set a number of the slices and a slice width common to each of the slices, the slice width being defined as a number of the slices multiplied by a slice thickness common to the each of the slices; and
a switch, provided in between the detector and the data acquisition unit, configured to switch a connection between the detecting elements and the data acquisition elements;
and wherein the controller is further configured to control the switch so as to keep the connection identical in both the pre-scan and the image scan even when the setting unit sets one of the number of the slices and the slice width to be different in between the pre-scan and the image scan.

32. The apparatus according to claim 31, wherein the controller is still further configured to control that the data output from at least a predetermined one of the detecting elements to at least one connected data acquisition element are not used in an image reconstruction by the reconstruction unit, the at least predetermined one of the detecting elements being not used in the pre-scan in accordance with the number of the slices and the slice width set by the setting unit.

33. The apparatus according to claim 29, wherein, when a plurality of slices are obtained in each single rotation of the pre-scan and the image scan, the controller is also configured to set a slice thickness common to each of the slices and a condition using the data acquisition elements to be common in both the pre-scan and the image scan, and further configured to set a different number of the detecting elements to be used in between the pre-scan and the image scan.

34. A method of performing a scan in an X-ray computed tomography apparatus, comprising steps of;
generating a first X-ray in a pre-scan mode;
detecting with an X-ray detector a first transmission X-ray exposed through a specimen to a first exposure width of the X-ray detector along a body axis of the specimen, resulting from the first X-ray at a first scanning position in the pre-scan mode;
displaying a first image based on the first transmission X-ray;
generating a second X-ray in an image scan mode;
detecting with the X-ray detector a second transmission X-ray exposed through the specimen to a second exposure width of the X-ray detector along the body axis of the specimen, resulting from the second X-ray at a second scanning position in the image scan mode, the second exposure width being wider than the first exposure width;
displaying a second image based on the second transmission X-ray; and
controlling the first scanning position and the second scanning position.

35. A computer program product on which is stored a computer program for performing a scan in an X-ray computed tomography apparatus, the computer program having instructions, which when executed, perform steps comprising:
generating a first X-ray in a pre-scan mode;
detecting with an X-ray detector a first transmission X-ray exposed through a specimen to a first exposure width of the X-ray detector along a body axis of the specimen, resulting from the first X-ray at a first scanning position in the pre-scan mode;
generating a second X-ray in an image scan mode;
displaying a first image based on the first transmission X-ray;
detecting with the X-ray detector a second transmission X-ray exposed through the specimen to a second exposure width of the X-ray detector long the body axis of the specimen, resulting from the second X-ray at a second scanning position in the image scan mode, the second exposure width being wider than the first exposure width;
displaying a second image based on the second transmission X-ray; and
controlling the first scanning position and the second scanning position.

* * * * *